United States Patent
Lange et al.

(10) Patent No.: US 10,583,078 B2
(45) Date of Patent: Mar. 10, 2020

(54) PRODUCT AND METHOD FOR THE TEMPORARY SHAPING OF KERATIN-CONTAINING FIBERS

(71) Applicant: Henkel AG & Co. KGaA, Duesseldorf (DE)

(72) Inventors: Julia Bibiane Lange, Bad Bramstedt (DE); Anna Puls, Winsen (DE); Cyrielle Martinez, Hamburg (DE); Bernd Richters, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 9 days.

(21) Appl. No.: 15/556,295

(22) PCT Filed: Nov. 11, 2015

(86) PCT No.: PCT/EP2015/076327
§ 371 (c)(1),
(2) Date: Sep. 7, 2017

(87) PCT Pub. No.: WO2016/142011
PCT Pub. Date: Sep. 15, 2016

(65) Prior Publication Data
US 2018/0042834 A1    Feb. 15, 2018

(30) Foreign Application Priority Data
Mar. 9, 2015   (DE) .......................... 10 2015 204 146

(51) Int. Cl.
*A61K 8/81* (2006.01)
*A61K 8/41* (2006.01)
*A61Q 5/06* (2006.01)

(52) U.S. Cl.
CPC .............. *A61K 8/8152* (2013.01); *A61K 8/41* (2013.01); *A61Q 5/06* (2013.01); *A61K 2800/594* (2013.01)

(58) Field of Classification Search
CPC .. A61K 2800/594; A61K 8/41; A61K 8/8152; A61Q 5/06
See application file for complete search history.

(56) References Cited

U.S. PATENT DOCUMENTS

| | | | |
|---|---|---|---|
| 2006/0251600 A1 | 11/2006 | Tamareselvy et al. | |
| 2009/0226390 A1 | 9/2009 | Birkel | |
| 2014/0093467 A1* | 4/2014 | Knappe | A61K 8/8152 424/70.15 |
| 2015/0004115 A1 | 1/2015 | Tan et al. | |
| 2018/0049967 A1* | 2/2018 | Lange | A61Q 5/06 |
| 2018/0055755 A1* | 3/2018 | Lange | A61Q 5/06 |
| 2018/0055756 A1* | 3/2018 | Lange | A61Q 5/06 |
| 2018/0055757 A1* | 3/2018 | Lange | A61Q 5/06 |
| 2018/0055758 A1* | 3/2018 | Lange | A61Q 5/06 |

FOREIGN PATENT DOCUMENTS

| | | | | |
|---|---|---|---|---|
| DE | 102007008089 A1 | | 8/2008 | |
| DE | 102011077364 | * | 12/2012 | .............. A61K 8/81 |
| EP | 1726331 A1 | | 11/2006 | |
| WO | 2010009956 A1 | | 1/2010 | |
| WO | WO 2013/072118 | * | 5/2013 | |

OTHER PUBLICATIONS

Carrefour-CMI (Bouncy Curls Styling Mousse, Jan. 2015) (Year: 2015).*
Rohm Haas (Aculyn 38, INCI name: Acrylate/Vinyl Neodeconate Crosspolymer, 2007) (Year: 2007).*
Ashland (Perfectly clear AquaStyle SH-100 polymer for consumer-desirable performance attributes in crystal clear hair gels; http://ashlandstylebook.com/wp-content/uploads/2015/01/ASH-PC7934_AquaStyle_SH_100_Brochure.pdf (Year: 2014).*
Dow Personal Care Portfolio (http://www.kalekimya.com/admin/hizmetler_dokuman/1427398856_Dow_Portfolio_for_Personal_Care.pdf 2014) (Year: 2014).*
EPO, International Search Report and Written Opinion issued in International Application No. PCT/EP2015/076327, dated Jan. 19, 2016.
Mintel, "Bone Curls Styling Mousse", www.gnpd.com.
Rohm and Haas, "ACULYN 38 Rheology Modifier", Sep. 2005.
Anonymous: "Ashland brings performance and style to crystal clear gel with AquaStyle(TM) (NYSE:ASH)", URL: http://investor.ashland.com/releasedetail.cfm?releaseid=836949, Apr. 2014 (Apr. 1, 2014), XP055205095, Wilmington, DE.

* cited by examiner

*Primary Examiner* — Anna R Falkowitz
(74) *Attorney, Agent, or Firm* — Lorenz & Kopf, LLP

(57) ABSTRACT

The disclosure relates to a cosmetic composition for the temporary shaping of hair, containing a combination of two specific anionic copolymers. The cosmetic composition provides an extremely good moisture resistance.

16 Claims, No Drawings

PRODUCT AND METHOD FOR THE TEMPORARY SHAPING OF KERATIN-CONTAINING FIBERS

CROSS-REFERENCE TO RELATED APPLICATION

This application is a U.S. National-Stage entry under 35 U.S.C. § 371 based on International Application No. PCT/EP2015/076327, filed Nov. 11, 2015 which was published under PCT Article 21(2) and which claims priority to German Application No. 102015204146.8, filed, Mar. 9, 2015 which are all hereby incorporated in their entirety by reference.

TECHNICAL FIELD

The present disclosure relates to a cosmetic composition for the temporary shaping of hair or for the temporary reshaping of keratinic fibers, particularly human hairs, comprising a combination of two specific anionic copolymers.

BACKGROUND

The temporary shaping of hair for a longer time, up to multiple days, typically requires the use of strengthening agents. Hair treatment agents that allow for the temporary shaping of hair play an important role.

Corresponding agents for temporary deformation typically contain synthetic polymers and/or waxes as a strengthening agent. Agents for supporting the temporary reshaping of keratin-containing fibers may be formulated for example as a hair spray, hair wax, hair gel, or hair foam.

The most important property of an agent for temporary deformation of hair, hereinafter also called a "styling agent," is that it may give the treated fibers the strongest possible hold on the newly modeled shape (i.e. a shape pressed onto the hair). This is also referred to as a strong hairstyle hold or a high degree of hold of the styling agent. The hairstyle hold is in essence determined by the kind and quantity of the strengthening substances that are used, although the other components of the styling agent may also have an influence.

In addition to a high degree of retention, styling agents must meet a wide range of other requirements. These may be broadly classified into properties with respect to the hair; properties of the relevant formulation, e.g. properties of the foam, gel, or sprayed aerosol; and properties that relate to handling the styling agent; the properties with respect to the hair are of particular importance. Of particular note are moisture resistance, low tack, and balanced conditioning effect. Further, a styling agent should to the extent possible be universally applicable to all hair types, and be mild on hair and skin.

In order to meet these various requirements, a great number of synthetic polymers have been developed as strengthening substances that are already being used in styling agents. These polymers may be classified as cationic, anionic, nonionic, and amphoteric strengthening polymers. Ideally, the polymers when applied to the hair yield a polymer film that imparts a strong hold to the hairstyle, but is also sufficiently flexible that it does not break under stress. If the polymer film is too brittle, film deposits, i.e. residues, arise that break off when the hair is moved and give the impression that the user of the styling agent has dandruff. Similar problems arise when waxes are used as a strengthening substance in the styling agent. If the styling agent is a gel or a paste, the polymers should also have thickening properties.

Known anionic polymers used in hair fixing products are copolymers having two or more structural units. Certain cross-linked copolymers of this kind, having the INCI name Acrylates/vinyl neodecanoate cross-polymers, as well as the use thereof in agents for temporarily deforming hair, are described in International Application WO 2010/009956 A1.

Further, hydrophobically modified copolymers (INCI: acrylate copolymers (and) water) are commercially available that act essentially as thickeners. The AquaStyle® SH-100 Polymer (Ashland Inc.) data sheet describes such a copolymer and its use in combination with carbomers. Therein are described a suitability for crystal-clear hair gels, a good initial stiffness, moisture resistance and a long-lasting effect.

One purpose as contemplated herein was to provide additional suitable polymer combinations that are distinguished by good film-forming and/or fixing properties, have a very high degree of hold without needing to give up flexibility and good moisture resistance, particularly sweat and water resistance; and are also suitable for the preparation of stably viscous and stably transparent cosmetic compositions. In particular, currently-available styling agents are still sufficiently capable of improvement that they do not always sufficiently ensure a good combination of stiffness and long-term retention (high humidity curl retention). It is accordingly one purpose as contemplated herein to provide styling agents of this kind, which in addition to the aforementioned properties, in particular provide both good stiffness and good long-lasting hold.

BRIEF SUMMARY

A cosmetic composition for temporarily reshaping keratinic fibers is provided herein. The cosmetic composition includes at least one cross-linked anionic copolymer (a). The at least one cross-linked anionic copolymer (a) includes at least one structural unit according to formula (a1),

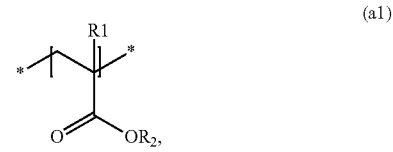

(a1)

where R1 is —H or —CH$_3$ and R2 is —H or —CH$_3$ or —CH$_2$CH$_3$ or —CH$_2$CH$_2$CH$_3$ or —CH(CH$_3$)$_2$. The at least one cross-linked anionic copolymer (a) further includes at least one further structural unit which is different from structural unit (a1) according to formula (a2),

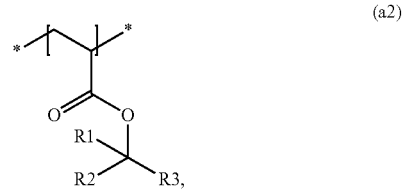

(a2)

where R1 and R2 are each independently H or —CH₃ or —CH₂CH₃ or —CH₂CH₂CH₃ or —CH(CH₃)₂ and R3 is a saturated or unsaturated, straight-chain or branched $C_{6-22}$ hydrocarbon radical.

The cosmetic composition further includes at least one anionic copolymer (b). The at least one anionic copolymer (b) includes at least the following monomer units: (b1) at least one (meth)acrylic acid ester unit, (b2) at least one ethyl (meth)acrylate unit, and (b3) at least one (meth)acrylic acid ester unit. The at least one (meth)acrylic acid ester unit (b3) is different from the ethyl (meth)acrylate unit (b2) and has a hydrophobic group as the ester group.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

This purpose was achieved as contemplated herein by a combination of two specific anionic copolymers.

The present disclosure provides:
1. A cosmetic composition for temporarily reshaping keratinic fibers, comprising:
   a) at least one cross-linked anionic copolymer (a), which:
   contains at least one structural unit according to formula (a1),

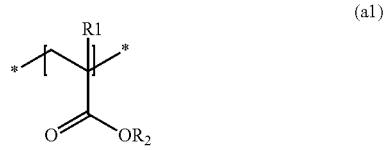

where R1 is —H or —CH3 and R2 is —H or —CH3 or —CH2CH3 or —CH₂CH₂CH₃ or —CH(CH₃)₂, and contains at least one further structural unit which is different from structural unit (a1) according to formula (a2),

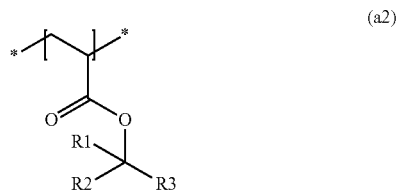

where R1 and R2 are each independently H or —CH₃ or —CH₂CH₃ or —CH₂CH₂CH₃ or —CH(CH₃)₂ and R3 is a saturated or unsaturated, straight-chain or branched $C_{6-22}$ hydrocarbon radical;
and
   (b) at least one anionic copolymer (b), which includes at least the following monomer units:
   (b1) at least one (meth)acrylic acid ester unit
   (b2) at least one ethyl (meth)acrylate unit
   (b3) at least one (meth)acrylic acid ester unit that is different from the ethyl (meth)acrylate unit (b2) and has a hydrophobic group as the ester group 2. A cosmetic composition according to Point 1, comprising:
   (a) at least one crosslinked copolymer (a) that includes at least the following monomer units:
      at least one (meth)acrylic acid unit,
      at least one vinylneodecanoate unit;
   and
   (b) at least one anionic copolymer (b) that includes at least one of the following monomer units:
      (b1) at least one (meth)acrylic acid ester unit
      (b2) at least one ethyl (meth)acrylate unit
      (b3) at least one (meth)acrylic acid ester unit that is different from the ethyl (meth)acrylate unit (b2) and has a hydrophobic group as the ester group.

3. A cosmetic composition according to one of the foregoing points, wherein the copolymer (a) is prepared by emulsion polymerization.

4. A cosmetic composition according to one of the foregoing points, wherein the composition contains the copolymer (a) in the proportion from about 0.05 to about 5.0 wt. %, preferably from about 0.5 to about 4.0 wt. %, particularly preferably from about 1.0 to about 3.0 wt. %, relative to the total weight of the cosmetic preparation.

5. Cosmetic composition according to one of the foregoing points, wherein the anionic copolymer (b) has methacrylic acid as monomer unit (b1) and ethylacrylate as monomer unit (b2).

6. Cosmetic composition according to one of the foregoing points, wherein the anionic copolymer (b) has an alkyl (meth)acrylate as monomer unit (b3).

7. Cosmetic composition according to one of the foregoing points, wherein the composition contains the anionic copolymer (b) in the proportion from about 0.05 to about 5.0 wt. %, preferably from about 0.5 to about 4.0 wt. %, particularly preferably from about 1.0 to about 3.0 wt. %, relative to the total weight of the cosmetic preparation.

8. Cosmetic composition according to one of the foregoing points, wherein the anionic copolymer (b) has a viscosity of from about 60000 to about 120000 cPs at a solid content of 2 wt. % in an aqueous neutralized solution at 25° C.

9. Cosmetic composition according to one of the foregoing points, wherein the anionic copolymer (a) has the INCI name copolymer a): Acrylates/Neodecanoate Crosspolymer, particularly Aculyn® 38 (Rohm & Haas).

10. Cosmetic composition according to one of the foregoing points, wherein the anionic copolymer (b) has the INCI name Acrylates Copolymer (and) Water, particularly AquaStyle SH-100 (Ashland Inc.).

11. Cosmetic composition according to one of the foregoing points, wherein the anionic copolymer (a) has the INCI name copolymer a): Acrylates/Neodecanoate Crosspolymer, and the anionic copolymer (b) has the INCI name Acrylates Copolymer (and) Water.

12. Cosmetic composition according to one of the foregoing points, wherein the anionic copolymer (a) is Aculyn® 38 (Rohm & Haas) and the anionic copolymer (b) is AquaStyle® SH-100 (Ashland Inc.)

13. Cosmetic composition according to one of the foregoing points, wherein the composition contains, relative to the total weight of the cosmetic preparation:
   from about 0.05 to about 5.0 wt. % of the anionic copolymer (a), and
   from about 0.05 to about 5.0 wt. % of the anionic copolymer (b).

14. Cosmetic composition according to one of the foregoing points, containing, relative to the total weight of the cosmetic preparation:

from about 1.0 to about 3.0 wt. % of the anionic copolymer (a), and
from about 1.0 to about 3.0 wt. % of the anionic copolymer (b).

15. Cosmetic composition according to one of the foregoing points, wherein the composition further comprises at least one polymer (c) that is different from the copolymers (a) and (b), and in particular comprises an anionic or nonionic polymer (c).

16. Cosmetic composition according to one of the foregoing points, exemplified in that it further comprises
  c) from about 1.0 to about 10 wt. % of polyvinylpyrrolidone and/or vinylpyrrolidone/vinyl acetate copolymer, preferably polyvinylpyrrolidone.

17. Cosmetic composition according to Point 16, exemplified in that the weight fraction of the polyvinylpyrrolidone and/or vinylpyrrolidone/vinyl acetate copolymer c), relative to the total weight of the cosmetic composition, is from about 2.0 to about 8.5 wt. %, and preferably from about 3.0 to about 7.0 wt. %.

18. Cosmetic composition according to one of the foregoing points, wherein the composition contains water in the amount of from about 50 to about 90%, preferably from about 60 to about 90 wt. %, and particularly preferably between about 65 and about 85 wt. %, relative to the total weight of the cosmetic preparation.

19. Cosmetic composition according to one of the foregoing points, wherein the composition is in the form of a hair gel, hair spray, hair foam or hair wax, particularly a hair gel.

20. Use of a cosmetic composition according to one of Points 1 through 19, for temporary reshaping of keratinic fibers.

21. Use of a cosmetic composition according to one of Points 1 through 19, for improving the moisture resistance of temporary deformed keratinic fibers.

22. Method for the temporary deformation of keratinic fibers, particularly human hair, wherein the cosmetic composition according to one of the points 1 through 19 is applied to keratinic fibers.

The following detailed description is merely exemplary in nature and is not intended to limit the disclosure or the application and uses of the subject matter as described herein. Furthermore, there is no intention to be bound by any theory presented in the preceding background or the following detailed description.

It was unexpectedly discovered in the context as contemplated herein that the moisture resistance of styling products may be improved by combining two known components that are already used in styling products. Other conventionally required properties of styling products, such as long-lasting hold, stiffness, and low tack, were still obtained in this case. Such a good combination of properties was not expected based on the knowledge of the individual components, and was surprising. It was shown experimentally that the combination of the two components resulted in a strongly overadditive, i.e. synergistic, effect with respect to moisture resistance, which was apparent in the HHRC (High Humidity Curl Retention) test.

Keratinic fibers for purposes as contemplated herein encompass furs, wool, and feathers, but particularly human hair.

The essential components of the cosmetic composition as contemplated herein are the crosslinked anionic copolymer (a) and the anionic copolymer (b) that is different from the copolymer (a).

The agents as contemplated herein contain, as a first required component, a crosslinked copolymer (a), which includes at least two different structural units having formulas (a1) and (a2). Additional structural units may also be present.

As a first structural unit, the crosslinked copolymer A comprises a unit of the formula (a1),

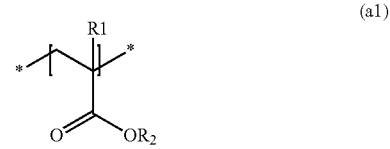

where R1 is —H or —$CH_3$ and R2 is —H or —$CH_3$ or —$CH_2CH_3$ or —$CH_2CH_2CH_3$ or —$CH(CH_3)_2$. If R1 represents —H, the monomers for the structural unit (a1) are acrylic acid or acrylic acid esters; if R1=—CH3, the monomers of structural unit (a1) are methacrylic acid or methacrylic esters. Very particularly preferred monomers for structural unit (a1) are acrylic acid, methacrylic acid, methyl acrylate, methyl methacrylate, ethyl acrylate, ethyl methacrylate, propyl acrylate, propyl methacrylate, isopropyl acrylate and isopropyl methacrylate.

Particularly preferred agents according to this disclosure include acrylic acid or acrylic acid ester as a monomer component in the copolymer (a). Such agents are exemplified in that the copolymer (a) contains structural units of formula (a1-1),

where R represents H or —$CH_3$ or —$CH_2CH_3$ or —$CH_2CH_2CH_3$ or —$CH(CH_3)_2$. Such copolymers (a) are particularly preferred where R is H. Particularly preferred copolymers (a) have structural units of the formula (a1-2).

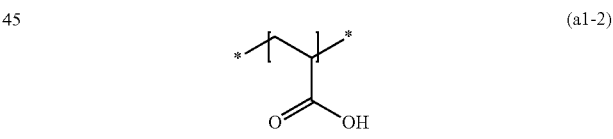

The additional structural unit present in the copolymer (a) may be represented by the formula (a2).

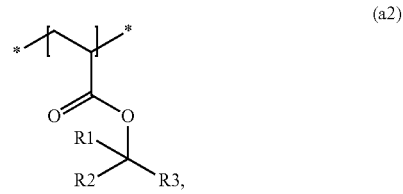

where R1 and R2 are each independently H or $CH_3$ or —$CH_2CH_3$ or —$CH_2CH_2CH_3$ or —$CH(CH_3)_2$ and R3 is a saturated or unsaturated, straight-chain or branched $C_{6-22}$ hydrocarbon radical. Among the compounds of the formula (a2), preference is given to those structural units for which R1=R2=H. Particularly preferred structural units (a2) can thus be described by the formulas (a2-1),

where R3 is a saturated or unsaturated, branched $C_{6-22}$ hydrocarbon radical, preferably a neoheptyl, neoctyl, neononyl or neodecyl radical.

Particularly preferred agents according to this disclosure are exemplified in that the copolymer (a) contains structural units of the formula (a2-2).

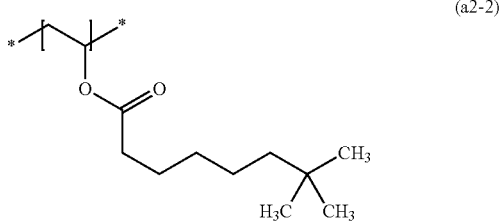

Preferably, the monomers of formulas (I) and (II) are present in copolymer (a) within a certain range. Preferred agents according to this disclosure are exemplified in that they contain copolymer(s) (a) that contain from 10 to 95 mol %, preferably from about 15 to about 85 mol %, and in particular from about 20 to about 80 mol %, of monomers of the formula (a1), and preferably (a1-2), and from about 5 to about 90 mol %, preferably from about 7.5 to about 80 mol % and in particular from about 10 to about 60 mol % of monomers of the formula (a2), preferably (a2-2).

Particularly preferred crosslinked copolymers (a) are prepared by polymerization of (meth)acrylic acid, vinyl neodecanoate and optionally further monomers; and in particular by polymerization of acrylic acid, vinylneodecanoate and optionally further monomers. Particularly preferred cross-linked copolymers (a) are prepared by emulsion polymerization of (meth)acrylic acid, vinyl neodecanoate and optionally further monomers; and in particular by emulsion polymerization of acrylic acid, vinylneodecanoate and optionally further monomers. The molecular weights of preferred cross-linked copolymers (a) are from about 10 to about 750 kDa, preferably from about 25 to about 500 kDa, more preferably from about 30 to about 400 kDa, and particularly from about 40 to about 250 kDa.

Suitable crosslinked copolymers (a) are commercially available under the INCI name Acrylates/Neodecanoate Crosspolymer. Most preferred is the cross-linked copolymer (a) Aculyn® 38 from Rohm & Haas. This has, in the commercially available form, a solids content of from about 28 to about 33 wt. % and a pH of from about 2.1 to about 3.2.

Particularly preferred cosmetic compositions for temporarily reshaping keratinic fibers comprise:
(a) at least one crosslinked copolymer (a) that includes at least the following monomer units:
(a1) at least one (meth)acrylic acid unit;
(a2) at least one vinylneodecanoate unit;
and
(b) at least one anionic copolymer (b) that includes at least one of the following monomer units:
(b1) at least one (meth)acrylic acid ester unit
(b2) at least one ethyl (meth)acrylate unit
(b3) at least one (meth)acrylic acid ester unit that is different from the ethyl (meth)acrylate unit (b2) and has a hydrophobic group as the ester group.

The cosmetic compositions as contemplated herein contain, as a second essential component, an anionic copolymer (b).

The anionic copolymer (b) includes at least the following monomer units: at least one (meth)acrylic acid ester unit (b1), at least one ethyl (meth)acrylate unit (b2), and at least one (meth)acrylic acid ester unit (b3) that is different from the ethyl (meth)acrylate unit (b2) and has a hydrophobic group as the ester group.

As contemplated herein, the copolymer (b) may contain additional monomer units. According to a preferred embodiment as contemplated herein, however, the copolymer (b) is composed only of the units (b1), (b2) and (b3); i.e. it includes units that are derived from these monomer units.

The at least one (meth)acrylic acid unit (b1) may be a methacrylic acid or acrylic acid unit; a methacrylic acid unit is preferred.

The at least one ethyl (meth)acrylate unit (b2) may be an ethyl methacrylate unit or an ethyl acrylate unit; an ethyl acrylate unit is preferred.

As contemplated herein, the at least one (meth)acrylic acid ester unit (b3) may be an alkyl (meth)acrylate unit. The alkyl group of the alkyl (meth)acrylate unit controls the hydrophobicity of the copolymer. The alkyl group is preferably a linear or branched alkyl group with 2 to 30 carbon atoms, and more preferably 3 to 12 carbon atoms. As contemplated herein, the hydrophobic group may also be a hydrophobic group other than an alkyl group, for example an aromatic hydrocarbon ester group. An example is a substituted or unsubstituted phenyl ester group or substituted or unsubstituted alkylene phenyl ester group, for example a benzyl ester group.

The viscosity of the anionic copolymer (b) used in the cosmetic composition preferably has a viscosity of at most about 60000 to about 120000 cPs at a solid content of 2 wt. % in an aqueous neutralized solution at 25° C.

Suitable anionic copolymers (b) are commercially available under the INCI designation "Acrylates Copolymer (and) Water." Most preferred for the anionic copolymer (b) is the AquaStyle® SH-100 polymer from Ashland, Inc. In its commercially available form, this has a solids content of from about 28 to about 32 wt. % and a pH of from about 2.1 to about 4.0.

The cosmetic composition of the present disclosure contains the cross-linked copolymer (a) and copolymer (b) in amounts which are customary and suitable for styling agents and which may be adapted for a specific application and formulation.

The composition according to this disclosure may for example contain copolymer (a) in the quantity of from about 0.05 to about 5.0 wt. %, relative to the total weight of the composition as contemplated herein. It is more preferred that the proportion of the copolymer (a) is from about 0.5 to about 4.0 wt. %, and particularly from about 1.0 to about 3.0 wt. %, respectively representing the solid content of the active substance in the cosmetic composition.

The cosmetic composition as contemplated herein contains copolymer (b), relative to the total weight of the cosmetic preparation, in the quantity of, for example: from about 0.05 to about 5.0 wt. %, and preferably from about 0.5 to about 4.0 wt. %, and more preferably from about 1.0 to about 3.0 wt. %, each of these respectively representing the solid content of the active substance in the cosmetic composition.

In addition to the aforementioned advantages, cosmetic compositions as contemplated herein are distinguished from alternative cosmetic agents, in particular, by an improved long-lasting hold. A weight ratio of the polymers a) and b) in the cosmetic compositions of from about 5:1 to about 1:5, preferably from about 3:1 to about 1:3 and in particular from about 2:1 to about 1:2, has been found to be particularly advantageous for the cosmetic properties of agents as contemplated herein.

In a particularly preferred embodiment as contemplated herein, the cosmetic composition contains, as the anionic copolymer (a), the copolymer commercially available under the name Aculyn® 38; and as the anionic copolymer (b), the copolymer commercially available under the name Aqua-Style® SH-100. In this combination, particularly good results were obtained with regard to combined stiffness and long-lasting hold. This polymer combination is particularly advantageous for styling products in gel form. Additional properties generally required for styling products, such as moisture resistance and low tack, are particularly well-achieved with this combination, particularly when formulated as a hair gel.

Copolymers (a) and (b) are preferably used in the cosmetic composition in a partially neutralized or neutralized form. For neutralization, at least one alkanolamine is preferably used. The alkanolamines that can be used as alkalizing agents as contemplated herein are preferably selected from primary amines with a C2-C6 alkyl skeleton containing at least one hydroxyl group. Particularly preferred alkanolamines are those selected from the group consisting of 2-aminoethan-1-ol (monoethanolamine), tris (2-hydroxyethyl)-amine (triethanolamine), 3-aminopropan-1-ol, 4-aminobutane-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, and 2-amino-2-methylpropane-1,3-diol. Alkanolamines which are very particularly preferred as contemplated herein are those selected from the group consisting of 2-aminoethan-1-ol, 2-amino-2-methylpropan-1-ol and 2-amino-2-methylpropane-1,3-diol. 2-amino-2-methylpropanol has been found to be a particularly suitable neutralizing agent. Preferred cosmetic compositions according to this disclosure therefore contain 2-amino-2-methylpropanol. 2-amino-2-methylpropanol is preferably used in compositions as contemplated herein in a quantity that does not exceed the quantity needed to neutralize the copolymers (a) and (b).

Preferably the quantity of 2-amino-2-methylpropanol used in the compositions as contemplated herein is from about 80 to 100%, particularly preferably from about 90 to 100%, and particularly from about 95 to 100%, of the quantity needed for complete neutralization of copolymers (a) and (b). In a preferred embodiment, the weight fraction of the 2-amino-2-methylpropanol is from about 0.05 to about 7.0 wt. % of the total weight of the cosmetic agent, and preferably from about 0.1 to about 5.0 wt. %, and particularly from about 0.1 to about 3.0 wt. %.

In summary, a preferred cosmetic composition for temporarily reshaping keratinic fibers comprises, relative to the total weight thereof:

(a) from about 0.5 to about 4.0 wt. % of at least one crosslinked copolymer (a) that includes at least the following monomer units:
    at least one (meth)acrylic acid unit,
    at least one vinylneodecanoate unit; and
(b) from about 0.5 to about 4.0 wt. % of at least one anionic copolymer (b) that includes at least one of the following monomer units:
    (b1) at least one (meth)acrylic acid unit,
    (b2) at least one ethyl (meth)acrylate unit,
    (b3) at least one (meth)acrylic acid ester unit that is different from the ethyl (meth)acrylate unit (b2) and has a hydrophobic group as the ester group.

Preferably, the cosmetic composition as contemplated herein contains one or more other components(s) that act as thickeners or gelling agents, and which are different from the copolymers (a) and (b), and which also support film formation. Examples of these are cationic, anionic, nonionic or amphoteric polymers. The weight fraction of these additional components with respect to the total weight of the cosmetic composition can be comparatively low, due to the presence of the components (a) and (b), for example: from about 0.02 to about 3 wt. %, and preferably from about 0.05 to about 1.5 wt. %, and more preferably from about 0.2 to about 0.8 wt. %.

Examples are Acrylamide/Ammonium Acrylate Copolymer, Acrylamides/DMAPA Acrylates/Methoxy PEG Methacrylate Copolymer, Acrylamidopropyltrimonium Chloride/Acrylamide Copolymer, Acrylamidopropyltrimonium Chloride/Acrylates Copolymer, Acrylates/Acetoacetoxyethyl Methacrylate Copolymer, Acrylates/Acrylamide Copolymer, Acrylates/Ammonium Methacrylate Copolymer, Acrylates/t-Butylacrylamide Copolymer, Acrylates/C1-2 Succinates/Hydroxyacrylates Copolymer, Acrylates/Lauryl Acrylate/Stearyl Acrylate/Ethylamine Oxide Methacrylate Copolymer, Acrylates/Octylacrylamide Copolymer, Acrylates/Octylacrylamide/Diphenyl Amodimethicone Copolymer, Acrylates/Stearyl Acrylate/Ethylamine Oxide Methacrylate Copolymer, Acrylates/VA Copolymer, Acrylates/VP Copolymer, Adipic Acid/Diethylenetriamine Copolymer, Adipic Acid/Dimethylaminohydroxypropyl Diethylenetriamine Copolymer, Adipic Acid/Epoxypropyl Diethylenetriamine Copolymer, Adipic Acid/Isophthalic Acid/Neopentyl Glycol/Trimethylolpropane Copolymer, Allyl Stearate/VA Copolymer, Aminoethylacrylate Phosphate/Acrylates Copolymer, Aminoethylpropanediol-Acrylates/Acrylamide Copolymer, Aminoethylpropanediol-AMPD-Acrylates/Diacetoneacrylamide Copolymer, Ammonium VA/Acrylates Copolymer, AMPD-Acrylates/Diacetoneacrylamide Copolymer, AMP-Acrylates/Allyl Methacrylate Copolymer, AMP-Acrylates/C1-18 Alkyl Acrylates/C1-8 Alkyl Acrylamide Copolymer, AMP-Acrylates/Diacetoneacrylamide Copolymer, AMP-Acrylates/Dimethylaminoethylmethacrylate Copolymer, *Bacillus*/Rice Bran Extract/Soybean Extract Ferment Filtrate, Bis-Butyloxyamodimethicone/PEG-60 Copolymer, Butyl Acrylate/Ethylhexyl Methacrylate Copolymer, Butyl Acrylate/Hydroxypropyl Dimethicone Acrylate Copolymer, Butylated PVP, Butyl Ester of Ethylene/MA Copolymer, Butyl Ester of PVM/MA Copolymer, Calcium/Sodium PVM/MA Copolymer, Corn Starch/Acrylamide/Sodium Acrylate Copolymer, Diethylene Glycolamine/Epichlorohydrin/Piperazine Copolymer, Dimethicone Crosspolymer, Diphenyl Amodimethicone, Ethyl Ester of PVM/MA Copolymer, Hydrolyzed Wheat Protein/PVP Crosspolymer, Isobutylene/Ethylmaleimide/Hydroxyethylmaleimide Copolymer, Isobutylene/MA Copolymer, Isobutylmethacrylate/Bis-Hydroxypropyl Dimethicone Acrylate Copolymer, Isopropyl Ester of PVM/MA Copolymer, Lauryl Acrylate Crosspolymer, Lauryl Methacrylate/Glycol Dimethacrylate Crosspolymer, MEA-Sulfite, Methacrylic Acid/Sodium Acrylamidomethyl Propane Sulfonate Copolymer, Methacryloyl Ethyl Betaine/Acrylates Copolymer, Octylacrylamide/Acrylates/Butylaminoethyl Methacrylate Copolymer, PEG/PPG-25/25 Dimethicone/Acrylates Copolymer, PEG-8/SMDI Copolymer, Polyacrylamide, Polyacrylate-6, Polybeta-Alanine/Glutaric Acid Crosspolymer, Polybutylene Terephthalate, Polyester-1, Polyethylacrylate, Polyethylene Terephthalate, Polymethacryloyl Ethyl Betaine, Polypentaerythrityl Terephthalate, Polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polysilicone-9, Polyurethane-1, Polyurethane-6, Polyurethane-10, Polyvinyl Acetate, Polyvinyl Butyral, Polyvinylcaprolactam, Polyvinylformamide, Polyvinyl Imidazolinium Acetate, Polyvinyl Methyl Ether, Potassium Butyl Ester of PVM/MA Copolymer, Potassium Ethyl Ester of PVM/MA Copolymer, PPG-70 Polyglyceryl-10 Ether, PPG-12/SMDI Copolymer, PPG-51/SMDI Copolymer, PPG-10 Sorbitol, PVM/MA Copolymer, PVP, PVP/VA/Itaconic Acid Copolymer, PVP/VA/Vinyl Propionate Copolymer, Rhizobian Gum, Rosin Acrylate, Shellac, Sodium Butyl Ester of PVM/MA Copolymer, Sodium Ethyl Ester of PVM/MA Copolymer, Sodium Polyacrylate, Sterculia *Urens* Gum, Terephthalic Acid/Isophthalic Acid/Sodium Isophthalic Acid Sulfonate/Glycol Copolymer, Trimethylolpropane Triacrylate, Trimethylsiloxysilylcarbamoyl Pullulan, VA/Crotonates Copolymer, VA/Crotonates/Methacryloxybenzophenone-1 Copolymer, VA/Crotonates/Vinyl Neodecanoate Copolymer, VA/Crotonates/Vinyl Propionate Copolymer, VA/DBM Copolymer, VA/Vinyl Butyl Benzoate/Crotonates Copolymer, Vinylamine/Vinyl Alcohol Copolymer, Vinyl Caprolactam/VP/Dimethylaminoethyl Methacrylate Copolymer, VP/Acrylates/Lauryl Methacrylate Copolymer, VP/Dimethylaminoethylmethacrylate Copolymer, VP/DMAPA Acrylates Copolymer, VP/Hexadecene Copolymer, VP/VA Copolymer, VP/Vinyl Caprolactam/DMAPA Acrylates Copolymer, Yeast Palmitate and Styrene/VP Copolymer.

Examples of nonionic polymers are:
Vinyl pyrrolidone/vinyl acetate copolymers as are marketed, for example, under the trade name Luviskol (BASF). Luviskol VA 64 and Luviskol VA 73, both of which are vinyl pyrrolidone/vinyl acetate copolymers, are particularly preferred nonionic polymers.
Cellulose ethers, such as hydroxypropylcellulose, hydroxyethylcellulose and methylhydroxypropylcellulose, which are for example marketed under the trade names Culminal and Benecel (AQUALON).
Shellac.
Polyvinyl pyrrolidones, which are marketed, for example, under the trade name Luviskol (BASF).
Siloxanes. These siloxanes may be water-soluble as well as water-insoluble. Both volatile and non-volatile siloxanes are suitable, "non-volatile siloxanes" referring to those compounds that have boiling point above 200° C. at normal pressure. Preferred siloxanes are polydialkylsiloxanes such as, for example, polydimethylsiloxane, polyalkylarylsiloxanes, such as, for example, polyphenylmethylsiloxane, ethoxylated polydialkylsiloxanes, and polydialkylsiloxanes that contain amine and/or hydroxy groups.
Glycosidically substituted silicones.

For the additional component that acts as a gelling agent, a homopolyacrylic acid (INCI: Carbomer) is preferred, which is commercially available in various forms under the name Carbopol®. The carbomer is preferably present in a proportion of from about 0.02 to about 3 wt. %, and preferably from about 0.05 to about 1.5 wt. %, and more preferably from about 0.2 to about 0.8 wt. %, relative to the total weight of the composition as contemplated herein.

Based on their cosmetic effect in combination with copolymers a) and b), the film-forming polymers preferably used as contemplated herein are, in particular, the polyvinylpyrrolidones (INCI name: PVP) and the vinylpyrrolidone/vinyl acetate copolymers (INCI name: VP/VA Copolymer); the weight fraction of these polymers is preferably limited to the range of from about 1.0 to about 10 wt. %. Particularly preferred cosmetic compositions as contemplated herein are therefore exemplified in that they also contain from about 1.0 to about 10 wt. % of polyvinylpyrrolidone and/or vinylpyrrolidone-vinyl acetate copolymer, preferably polyvinylpyrrolidone, relative to the total weight of the composition. Particularly preferred cosmetic compositions have a weight fraction of polyvinylpyrrolidone and/or vinylpyrrolidone-nonyl acetate copolymer c), with respect to the total weight of the cosmetic composition, of from about 2.0 to about 8.5 wt. %, and preferably from about 3.0 to about 7.0 wt. %.

The cosmetic composition as contemplated herein may contain further conventional substances for styling products. Further suitable auxiliaries and additives include, in particular, additional care substances.

The agent may comprise, for example, at least one protein hydrolyzate and/or a derivative thereof as a care substance. Protein hydrolyzates are product mixtures that are obtained by the acid-, base- or enzyme-catalyzed degradation of proteins. In the context of the disclosure, the term "protein hydrolysates" covers total hydrolysates, as well as individual amino acids and derivatives thereof, and mixtures of different amino acids. The molecular weight of the protein hydrolysates that may be used as contemplated herein ranges from about 75 daltons, the molecular weight of glycine, to about 200,000 daltons; preferably, the molecular weight is from about 75 to about 50,000, and particularly preferably, from about 75 to about 20,000 daltons.

The composition as contemplated herein may further comprise, as a care substance, at least one vitamin, one provitamin, one vitamin precursor and/or a derivative of these. As contemplated herein, preference is given to those vitamins, provitamins and vitamin precursors that are usually assigned to groups A, B, C, E, F and H.

Like the addition of glycerol and/or propylene glycol, the addition of panthenol increases the flexibility of the polymer film that is formed when the composition as contemplated herein is used.

The compositions as contemplated herein may further comprise at least one plant extract, but also mono- or oligosaccharides and/or lipids.

Oil bodies are also suitable as care substances. Natural and synthetic cosmetic oil bodies include, for example, vegetable oils, liquid paraffin oils, isoparaffin oils and synthetic hydrocarbons and di-n-alkyl ethers with a total of between 12 and 36 carbon atoms, and particularly 12 to 24 carbon atoms. Preferred cosmetic compositions as contemplated herein contain at least one oil body, and preferably at least one oil body from the group of silicone oils. The group of silicone oils includes in particular the dimethicones, including also the cyclomethicones; the aminofunctional silicones; and the dimethiconols. The dimethicones may be either linear or branched, and may also be cyclic or cyclic and branched. Suitable silicone oils or silicone gums are, in particular, dialkyl- and alkylarylsiloxanes, such as dimethylpolysiloxane and methylphenylpolysiloxane, and also their alkoxylated, quaternized or anionic derivatives. Preferred are cyclic and linear polydialkylsiloxanes, their alkoxylated and/or aminated derivatives, dihydroxypolydimethylsiloxanes and polyphenylalkylsiloxanes.

Additional preferred oil bodies for care substances include esters of C6-C30 fatty acids with C2-C30 fatty alcohols, preferably monoesters of fatty acids with alcohols having 2 to 24 carbon atoms, such as isopropyl myristate (Rilanit® IPM), isononanoic acid-C16-18-alkyl ester (Cetiol® SN), 2-ethylhexyl palmitate (Cegesoft® 24), 2-ethylhexyl stearate (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleates (Cetiol®), hexyl laurates (Cetiol® A), di-n-butyl adipate (Cetiol® B), myristyl myristate (Cetiol® MM), cetearyl isononanoates (Cetiol® SN), and decyl oleate (Cetiol® V).

Further suitable care substances are dicarboxylic acid esters; symmetrical, asymmetrical or cyclic esters of carbonic acids with fatty alcohols; and trifatty acid esters of saturated and/or unsaturated linear and/or branched fatty acids with glycerol or fatty acid partial glycerides, including monoglycerides, diglycerides and technical mixtures thereof.

Furthermore, emulsifiers or surfactants are also preferably included in the composition as contemplated herein. Preference is given to PEG derivatives of hydrogenated castor oil, which may be obtained, for example, under the designation PEG Hydrogenated Castor Oil, for example PEG-30 Hydrogenated Castor Oil, PEG-33 Hydrogenated Castor Oil, PEG-35 Hydrogenated Castor Oil, PEG-36 Hydrogenated Castor Oil or PEG-40 Hydrogenated Castor Oil. As contemplated herein, the use of PEG-40 Hydrogenated Castor Oil is preferred. These are preferably present in an amount of from about 0.05 to about 1.5 wt. %, more preferably from about 0.1 to about 1.0 wt. %, and also preferably from about 0.2 to about 0.8 wt. % or from about 0.3 to about 0.6 wt. %.

The cosmetic compositions as contemplated herein contain the active ingredients in a cosmetically acceptable carrier.

Preferred cosmetically acceptable carriers are aqueous, alcoholic or aqueous-alcoholic media, preferably with at least about 10 wt. % water, calculated relative to the total weight of the composition.

It is particularly preferred that the cosmetic carrier as contemplated herein contains water in an amount, with respect to the total weight of the cosmetic agent, of at least about 10 wt. %, in particular at least about 20.0 wt. %, and most preferably at least about 40 wt. %. Very particularly preferred cosmetic compositions have a water content of between about 50 and about 95 wt. %, preferably between about 60 and about 90 wt. % and in particular between about 65 and about 85 wt. %, with respect to the total weight of the composition.

Alcohols that may be used are, in particular, the lower alcohols customarily used for cosmetic purposes, having from 1 to 4 carbon atoms, for example ethanol and isopropanol.

Examples of water-soluble solvents as cosolvents are glycerol and/or ethylene glycol and/or 1,2-propylene glycol in an amount of from 0 to about 30 wt. %, with respect to the total composition.

Tabular Overview

The composition of certain preferred cosmetic compositions may be found in the following tables (amounts in wt. % are based on the total weight of the cosmetic product, unless otherwise stated).

|  | Formula 1 | Formula 2 | Formula 3 | Formula 4 | Formula 5 |
| --- | --- | --- | --- | --- | --- |
| Copolymer a) | 0.05 to 5.0 | 0.5 to 4.0 | 0.5 to 3.0 | 0 to 4.0 | 1.0 to 3.0 |
| Copolymer b) | 0.05 to 5.0 | 0.05 to 5.0 | 0.5 to 4.0 | 5 to 4.0 | 1.0 to 3.0 |
| Misc | add 100 | add 100 | add 100 | add 100 | add 100 |

|  | Formula 1a | Formula 2a | Formula 3a | Formula 4a | Formula 5a |
| --- | --- | --- | --- | --- | --- |
| Copolymer a): Acrylates/ Neodecanoate Crosspolymer | 0.05 to 5.0 | 0.5 to 4.0 | 0.5 to 4.0 | 1.0 to 3.0 | 1.0 to 3.0 |
| Copolymer b): Acrylates Copolymer (and) Water | 0.05 to 5.0 | 0.05 to 5.0 | 0.5 to 4.0 | 0.5 to 4.0 | 1.0 to 3.0 |
| Misc | add 100 | add 100 | add 100 | add 100 | add 100 |

|  | Formula 1b | Formula 2b | Formula 3b | Formula 4b | Formula 5b |
| --- | --- | --- | --- | --- | --- |
| Copolymer a): Aculyn ® 38 (Rohm&Haas) (Given as solid content) | 0.05 to 5.0 | 0.5 to 4.0 | 0.5 to 4.0 | 1.0 to 3.0 | 1.0 to 3.0 |

|  | Formula 1b | Formula 2b | Formula 3b | Formula 4b | Formula 5b |
|---|---|---|---|---|---|
| Copolymer b): AquaStyle ® SH-100 (Given as solid content) | 0.05 to 5.0 | 0.05 to 5.0 | 0.5 to 4.0 | 0.5 to 4.0 | 1.0 to 3.0 |
| Misc | add 100 | add 100 | add 100 | add 100 | add 100 |

|  | Formula 6 | Formula 7 | Formula 8 | Formula 9 | Formula 10 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 6a | Formula 7a | Formula 8a | Formula 9a | Formula 10a |
|---|---|---|---|---|---|
| Copolymer a): Acrylates/Neodecanoate Crosspolymer | 0.05 to 5.0 | 0.5 to 4.0 | 0.5 to 4.0 | 1.0 to 3.0 | 1.0 to 3.0 |
| Copolymer b): Acrylates Copolymer (and) Water | 0.05 to 5.0 | 0.05 to 5.0 | 0.5 to 4.0 | 0.5 to 4.0 | 1.0 to 3.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 6b | Formula 7b | Formula 8b | Formula 9b | Formula 10b |
|---|---|---|---|---|---|
| Copolymer a): Aculyn ® 38 (Rohm&Haas) (Given as solid content) | 0.05 to 5.0 | 0.5 to 4.0 | 0.5 to 4.0 | 1.0 to 3.0 | 1.0 to 3.0 |
| Copolymer b): AquaStyle ® SH-100 (Given as solid content) | 0.05 to 5.0 | 0.05 to 5.0 | 0.5 to 4.0 | 0.5 to 4.0 | 1.0 to 3.0 |
| Polyvinylpyrrolidone | 1.0 to 10 | 2.0 to 8.5 | 2.0 to 8.5 | 3.0 to 7.0 | 3.0 to 7.0 |
| Misc/ | add 100 | add 100 | add 100 | add 100 | add 100 |

|  | Formula 11 | Formula 12 | Formula 13 | Formula 14 | Formula 15 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 11a | Formula 12a | Formula 13a | Formula 14a | Formula 15a |
|---|---|---|---|---|---|
| Copolymer a): Acrylates/Neodecanoate Crosspolymer | 0.05 to 5.0 | 0.5 to 4.0 | 0.5 to 4.0 | 1.0 to 3.0 | 1.0 to 3.0 |
| Copolymer b): Acrylates Copolymer (and) Water | 0.05 to 5.0 | 0.05 to 5.0 | 0.5 to 4.0 | 0.5 to 4.0 | 1.0 to 3.0 |

-continued

|  | Formula 11a | Formula 12a | Formula 13a | Formula 14a | Formula 15a |
|---|---|---|---|---|---|
| Vinylpyrrolidone/vinyl acetate copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 11b | Formula 12b | Formula 13b | Formula 14b | Formula 15b |
|---|---|---|---|---|---|
| Copolymer a): Aculyn ® 38 (Rohm&Haas) (Given as solid content) | 0.05 to 5.0 | 0.5 to 4.0 | 0.5 to 4.0 | 1.0 to 3.0 | 1.0 to 3.0 |
| Copolymer b): AquaStyle ® SH-100 (Given as solid content) | 0.05 to 5.0 | 0.05 to 5.0 | 0.5 to 4.0 | 0.5 to 4.0 | 1.0 to 3.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 16 | Formula 17 | Formula 18 | Formula 19 | Formula 20 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.05 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

|  | Formula 16a | Formula 17a | Formula 18a | Formula 19a | Formula 20a |
|---|---|---|---|---|---|
| Copolymer a): Acrylates/Neodecanoate Crosspolymer | 0.05 to 5.0 | 0.5 to 4.0 | 0.5 to 4.0 | 1.0 to 3.0 | 1.0 to 3.0 |
| Copolymer b): Acrylates Copolymer (and) Water | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

|  | Formula 16b | Formula 17b | Formula 18b | Formula 19b | Formula 20b |
|---|---|---|---|---|---|
| Copolymer a): Aculyn ® 38 (Rohm&Haas) (Given as solid content) | 0.05 to 5.0 | 0.5 to 4.0 | 0.5 to 4.0 | 1.0 to 3.0 | 1.0 to 3.0 |
| Copolymer b): AquaStyle ® SH-100 (Given as solid content) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

|  | Formula 21 | Formula 22 | Formula 23 | Formula 24 | Formula 25 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |

|  | Formula 21 | Formula 22 | Formula 23 | Formula 24 | Formula 25 |
|---|---|---|---|---|---|
| PEG-40 Hydrogenated Castor Oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

|  | Formula 21a | Formula 22a | Formula 23a | Formula 24a | Formula 25a |
|---|---|---|---|---|---|
| Copolymer a): Acrylates/Neodecanoate Crosspolymer | 0.05 to 5.0 | 0.5 to 4.0 | 0.5 to 4.0 | 1.0 to 3.0 | 1.0 to 3.0 |
| Copolymer b): Acrylates Copolymer (and) Water | 0.05 to 5.0 | 0.05 to 5.0 | 0.5 to 4.0 | 0.5 to 4.0 | 1.0 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

|  | Formula 21b | Formula 22b | Formula 23b | Formula 24b | Formula 25b |
|---|---|---|---|---|---|
| Copolymer a): Aculyn ® 38 (Rohm&Haas) (Given as solid content) | 0.05 to 5.0 | 0.5 to 4.0 | 0.5 to 4.0 | 1.0 to 3.0 | 1.0 to 3.0 |
| Copolymer b): AquaStyle ® SH-100 (Given as solid content) | 0.05 to 5.0 | 0.05 to 5.0 | 0.5 to 4.0 | 0.5 to 4.0 | 1.0 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

|  | Formula 26 | Formula 27 | Formula 28 | Formula 29 | Formula 30 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Water | 50 to 95 | 50 to 95 | 60 to 90 | 60 to 90 | 65 to 85 |
| Misc | add 100 | add 100 | add 100 | add 100 | add 100 |

|  | Formula 26a | Formula 27a | Formula 28a | Formula 29a | Formula 30a |
|---|---|---|---|---|---|
| Copolymer a): Acrylates/Neodecanoate Crosspolymer | 0.05 to 5.0 | 0.5 to 4.0 | 0.5 to 4.0 | 1.0 to 3.0 | 1.0 to 3.0 |
| Copolymer b): Acrylates Copolymer (and) Water | 0.05 to 5.0 | 0.05 to 5.0 | 0.5 to 4.0 | 0.5 to 4.0 | 1.0 to 3.0 |
| Water | 50 to 95 | 50 to 95 | 60 to 90 | 60 to 90 | 65 to 85 |
| Misc | add 100 | add 100 | add 100 | add 100 | add 100 |

|  | Formula 26b | Formula 27b | Formula 28b | Formula 29b | Formula 30b |
|---|---|---|---|---|---|
| Copolymer a): Aculyn ® 38 (Rohm&Haas) (Given as solid content) | 0.05 to 5.0 | 0.5 to 4.0 | 0.5 to 4.0 | 1.0 to 3.0 | 1.0 to 3.0 |
| Copolymer b): AquaStyle ® SH-100 (Given as solid content) | 0.05 to 5.0 | 0.05 to 5.0 | 0.5 to 4.0 | 0.5 to 4.0 | 1.0 to 3.0 |
| Water | 50 to 95 | 50 to 95 | 60 to 90 | 60 to 90 | 65 to 85 |
| Misc | add 100 | add 100 | add 100 | add 100 | add 100 |

|  | Formula 31 | Formula 32 | Formula 33 | Formula 34 | Formula 35 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 5 to 4.0 | 1.0 to 3.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 31a | Formula 32a | Formula 33a | Formula 34a | Formula 35a |
|---|---|---|---|---|---|
| Copolymer a): Acrylates/ Neodecanoate Crosspolymer | 0.05 to 5.0 | 0.5 to 4.0 | 0.5 to 4.0 | 1.0 to 3.0 | 1.0 to 3.0 |
| Copolymer b): Acrylates Copolymer (and) Water | 0.05 to 5.0 | 0.05 to 5.0 | 0.5 to 4.0 | 0.5 to 4.0 | 1.0 to 3.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 31b | Formula 32b | Formula 33b | Formula 34b | Formula 35b |
|---|---|---|---|---|---|
| Copolymer a): Aculyn ® 38 (Rohm&Haas) (Given as solid content) | 0.05 to 5.0 | 0.5 to 4.0 | 0.5 to 4.0 | 1.0 to 3.0 | 1.0 to 3.0 |
| Copolymer b): AquaStyle ® SH-100 (Given as solid content) | 0.05 to 5.0 | 0.05 to 5.0 | 0.5 to 4.0 | 0.5 to 4.0 | 1.0 to 3.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36 | Formula 37 | Formula 38 | Formula 39 | Formula 40 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Vinylpyrrolidone/ vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36a | Formula 37a | Formula 38a | Formula 39a | Formula 40a |
|---|---|---|---|---|---|
| Copolymer a): Acrylates/ Neodecanoate Crosspolymer | 0.05 to 5.0 | 0.5 to 4.0 | 0.5 to 4.0 | 1.0 to 3.0 | 1.0 to 3.0 |
| Copolymer b): Acrylates Copolymer (and) Water | 0.05 to 5.0 | 0.05 to 5.0 | 0.5 to 4.0 | 0.5 to 4.0 | 1.0 to 3.0 |
| Vinylpyrrolidone/ vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36b | Formula 37b | Formula 38b | Formula 39b | Formula 40b |
|---|---|---|---|---|---|
| Copolymer a): Aculyn ® 38 (Rohm&Haas) (Given as solid content) | 0.05 to 5.0 | 0.5 to 4.0 | 0.5 to 4.0 | 1.0 to 3.0 | 1.0 to 3.0 |
| Copolymer b): AquaStyle ® SH-100 (Given as solid content) | 0.05 to 5.0 | 0.05 to 5.0 | 0.5 to 4.0 | 0.5 to 4.0 | 1.0 to 3.0 |
| Vinylpyrrolidone/ vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 41 | Formula 42 | Formula 43 | Formula 44 | Formula 45 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 41a | Formula 42a | Formula 43a | Formula 44a | Formula 45a |
|---|---|---|---|---|---|
| Copolymer a): Acrylates/ Neodecanoate Crosspolymer | 0.05 to 5.0 | 0.5 to 4.0 | 0.5 to 4.0 | 1.0 to 3.0 | 1.0 to 3.0 |
| Copolymer b): Acrylates Copolymer (and) Water | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 41b | Formula 42b | Formula 43b | Formula 44b | Formula 45b |
|---|---|---|---|---|---|
| Copolymer a): Aculyn ® 38 (Rohm&Haas) (Given as solid content) | 0.05 to 5.0 | 0.5 to 4.0 | 0.5 to 4.0 | 1.0 to 3.0 | 1.0 to 3.0 |
| Copolymer b): AquaStyle ® SH-100 (Given as solid content) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 46 | Formula 47 | Formula 48 | Formula 49 | Formula 50 |
|---|---|---|---|---|---|
| Copolymer a) | 0.05 to 5.0 | 0.5 to 4.0 | 0.5 to 4.0 | 1.0 to 3.0 | 1.0 to 3.0 |
| Copolymer b) | 0.05 to 5.0 | 0.05 to 5.0 | 0.5 to 4.0 | 0.5 to 4.0 | 1.0 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

|  | Formula 46a | Formula 47a | Formula 48a | Formula 49a | Formula 50a |
|---|---|---|---|---|---|
| Copolymer a): Acrylates/ Neodecanoate Crosspolymer | 0.05 to 5.0 | 0.5 to 4.0 | 0.5 to 4.0 | 1.0 to 3.0 | 1.0 to 3.0 |
| Copolymer b): Acrylates Copolymer (and) Water | 0.05 to 5.0 | 0.05 to 5.0 | 0.5 to 4.0 | 0.5 to 4.0 | 1.0 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

|  | Formula 46b | Formula 47b | Formula 48b | Formula 49b | Formula 50b |
|---|---|---|---|---|---|
| Copolymer a): Aculyn ® 38 (Rohm&Haas) (Given as solid content) | 0.05 to 5.0 | 0.5 to 4.0 | 0.5 to 4.0 | 1.0 to 3.0 | 1.0 to 3.0 |
| Copolymer b): AquaStyle ® SH-100 (Given as solid content) | 0.05 to 5.0 | 0.05 to 5.0 | 0.5 to 4.0 | 0.5 to 4.0 | 1.0 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

In the context of this disclosure, "Misc" refers to a cosmetic carrier, in particular (unless separately indicated) water, and optionally to further conventional components of styling products.

The cosmetic composition as contemplated herein may be formulated in the forms that are conventional for temporary reshaping of hair, e.g. as a hair gel, hair spray, hair foam or hair wax. Formulation as a hair gel is preferred.

Both hair foams and hair sprays require the presence of propellants. But as contemplated herein, it is preferable that no hydrocarbons, or only limited quantities, should be used. As contemplated herein, propane, propane/butane mixtures, and dimethyl ether are particularly suitable propellants.

The present disclosure also relates to the use of cosmetic compositions as contemplated herein for the temporary reshaping of keratinic fibers, particularly human hair, as well as to a method for the temporary deformation of keratinic fibers, particularly human hair, wherein the cosmetic composition as contemplated herein is applied to keratinic fibers.

A further purpose of this patent application is the use of a cosmetic composition as contemplated herein for improving the moisture resistance of temporary deformed keratinic fibers.

Examples

The following hair gels were prepared:

| Component/raw material | INCI name or chemical name | V1 | V2 | E1 |
|---|---|---|---|---|
| Aculyn ® 38 [1] | Acrylates/Neodecanoate Crosspolymer | 3.3 | — | 1.65 |
| AquaStyle SH-100 [2] | Acrylates Copolymer (and) Water | — | 3.3 | 1.65 |
| AMP-ULTRA PC 2000 | Aminomethyl Propanol | 0.3 | 0.3 | 0.3 |
| Water |  | 94.6 | 94.6 | 94.6 |
| Total |  | 100 | 100 | 100 |

[1] 30 wt. % active substance in water
[2] 30 wt. % active substance in water

The quantities provided in the table are given in the wt. % of the respective raw material, relative to the total composition. The polymer content in each of compositions V1, V2 and E1 was 1.0 wt. %.

For the resulting styling agents, moisture resistance was determined by employing an HHCR test (High Humidity Curl Retention Test: 6 h) on cleaned Kerling hair strands (mean value for 5 hair strands):

|      | V1  | V2  | E1  |
| ---- | --- | --- | --- |
| HHCR | 78% | 78% | 87% |

The polymer combination E1 as contemplated herein accordingly showed a markedly overadditive, synergistic effect with regard to moisture resistance.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Cosmetic composition for temporarily reshaping keratinic fibers, consisting of:
   a cross-linked anionic copolymer (a), which consists of;
   at least one structural unit according to formula (a1),

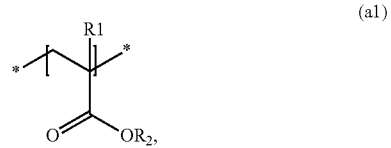

where R1 is —H or —CH$_3$ and R2 is —H or —CH$_3$ or —CH$_2$CH$_3$ or —CH$_2$CH$_2$CH$_3$ or —CH(CH$_3$)$_2$, and
at least one further structural unit which is different from structural unit (a1) according to formula (a2),

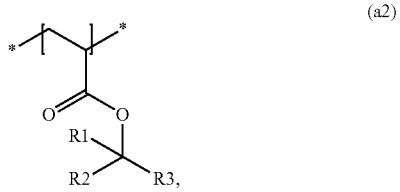

where R1 and R2 are each independently H or —CH$_3$ or —CH$_2$CH$_3$ or —CH$_2$CH$_2$CH$_3$ or —CH(CH$_3$)$_2$ and R3 is a saturated or unsaturated, straight-chain or branched C$_{6-22}$ hydrocarbon radical;
at least one anionic copolymer (b), which consists of the following monomer units;
   (b1) at least one methacrylic acid unit,
   (b2) at least one ethyl_acrylate unit, and
   (b3) at least one alkyl (meth)acrylate;
at least one alkanolamine;
water in a proportion of at least 40% by weight with respect to the total weight of the cosmetic composition; and
optionally, at least one polymer (c) chosen from polyvinyl pyrrolidone, vinyl pyrrolidone/vinyl acetate copolymer, at least one PEG derivative of hydrogenated castor oil, or homopolyacrylic acid.

2. Cosmetic composition according to claim 1, wherein the composition comprises the copolymer (a) in the proportion from about 0.05 to about 5.0 wt. % and the anionic copolymer (b) in the proportion from about 0.05 to about 5.0 wt. %, wherein all amounts are relative to the total weight of the cosmetic preparation.

3. Cosmetic composition according to claim 1, wherein the composition is in the form of a hair gel, hair spray, hair foam or hair wax.

4. Cosmetic composition according to claim 1, wherein the cosmetic composition is utilized for temporary reshaping of keratinic fibers.

5. Method for the temporary deformation of keratinic fibers, the method comprising applying the cosmetic composition according to claim 1 to keratinic fibers.

6. Cosmetic composition according to claim 1, wherein the copolymer (a) is prepared by emulsion polymerization.

7. Cosmetic composition according to claim 1, wherein the anionic copolymer (b) has a viscosity of from about 60000 to about 120000 cPs at a solid content of 2 wt. % in an aqueous neutralized solution at 25° C.

8. Cosmetic composition according to claim 1, wherein the anionic copolymer (a) has the INCI name copolymer acrylates/neodecanoate crosspolymer.

9. Cosmetic composition according to claim 1, wherein the anionic copolymer (b) has the INCI name acrylates copolymer (and) water.

10. Cosmetic composition according to claim 1, wherein the at least one polymer (c) is present in an amount of from about 1.0 to about 10 wt. % and is chosen from polyvinylpyrrolidone, vinylpyrrolidone/vinyl acetate copolymer, or a combination thereof.

11. Cosmetic composition according to claim 1, wherein the cosmetic composition includes water in the amount of at least about 65%, relative to the total weight of the cosmetic composition.

12. Cosmetic composition according to claim 5, wherein the at least one alkanolamine comprises 2-aminoethan-1-ol, 2-amino-2-methylpropan-1-ol, 2-amino-2-methyl-propan-1,3-diol, or combinations thereof.

13. The cosmetic composition of claim 1, wherein the at least one copolymer (a) consists of (a1) at least one (meth)acrylic acid unit, and (a2) at least one vinylneodecanoate unit.

14. The cosmetic composition of claim 13, wherein the at least one copolymer (b) consists of the following monomer units:
   (b1) at least one methacrylic acid unit,
   (b2) at least one ethyl acrylate unit, and
   (b3) at least one (meth)acrylic acid alkyl ester unit which is different from the ethyl acrylate unit (b2) and which has a hydrophobic group as an ester group.

15. The cosmetic composition of claim 14, wherein the composition comprises the copolymer (a) in a proportion of from about 0.05% to about 5.0% by weight with respect to the total weight of the cosmetic composition.

16. The cosmetic composition of claim 15, wherein the composition comprises the copolymer (b) in a proportion of from about 0.05 to about 5.0% by weight with respect to the total weight of the cosmetic composition.

* * * * *